United States Patent [19]
Morikawa et al.

[11] Patent Number: 6,018,048
[45] Date of Patent: Jan. 25, 2000

[54] NOBLE METAL RANEY CATALYSTS AND PREPARATION OF HYDROGENATED COMPOUNDS THEREWITH

[75] Inventors: Kouhei Morikawa; Shuuji Hirayama; Yoshimasa Ishimura; Yuseki Suyama; Tsutomu Nozawa; Hiroyuki Monzen; Motoo Miura; Kuniomi Marumo; Taketoshi Naito, all of Kawasaki, Japan

[73] Assignee: Showa Denko K.K., Tokyo, Japan

[21] Appl. No.: 08/989,157

[22] Filed: Dec. 11, 1997

Related U.S. Application Data

[62] Division of application No. 08/582,668, Jan. 4, 1996, abandoned.

[30] Foreign Application Priority Data

Jan. 6, 1995 [JP] Japan ........................................... 7-782

[51] Int. Cl.⁷ ............................ C07D 211/02; C07C 5/02
[52] U.S. Cl. ........................................... 546/185; 585/277
[58] Field of Search ........................... 502/301; 585/277; 546/185

[56] References Cited

U.S. PATENT DOCUMENTS

| | | |
|---|---|---|
| 2,014,867 | 9/1935 | Schrauth . |
| 2,776,293 | 1/1957 | Levy et al. . |
| 3,431,220 | 3/1969 | Batzold . |
| 3,544,485 | 12/1970 | Taira . |
| 4,070,399 | 1/1978 | Butte, Jr. ................................. 260/563 |
| 4,513,149 | 4/1985 | Gray et al. . |
| 5,536,694 | 7/1996 | Schuetz et al. . |

FOREIGN PATENT DOCUMENTS

| | | |
|---|---|---|
| 6-279368 | 4/1994 | Japan . |
| 1358785 | 7/1974 | United Kingdom . |

OTHER PUBLICATIONS

Hawley, G. G.; Ed.; Condensed Chemical Dictionary, Ninth Ed.; Van Nostrand Reinhold, NY, 1977.
Smirnova et al.; Issled. Obl. Geterotsilk. Soedin. 1971 pp. 5–14. CA 77:79918.
Rylander, P. N.; Hydrogenation Methods; Academic Press, London; 1985.

*Primary Examiner*—Gary Geist
*Assistant Examiner*—Robert W. Deemie
*Attorney, Agent, or Firm*—Sughrue, Mion, Zinn, Macpeak & Seas, PLLC

[57] ABSTRACT

Noble metal, particularly ruthenium, Raney catalysts having the property of catalyzing the hydrogenation of (1) aromaticity-exhibiting ring portions of organic compounds, (2) carboxylic acids and their ester portions (carbonyl ester groups), (3) ring portions and carboxylic acid or their ester groups in compounds having such ring portions and carboxylic acid or their ester portions, and (4) ring portions and nitrile groups of aromatic nitrile compounds and methods for the preparation of corresponding hydrogenated compounds. The methods allow preparation of hydrogenated compounds having hydrogenated aromatic ring portions, hydrogenated carbonyl ester groups, hydrogenated aromatic ring and carbonyl ester groups, or hydrogenated aromatic rings and nitrile groups under milder hydrogen pressure and temperature conditions than the conventional catalysts.

4 Claims, No Drawings

NOBLE METAL RANEY CATALYSTS AND PREPARATION OF HYDROGENATED COMPOUNDS THEREWITH

CROSS REFERENCE OF APPLICATION

This is a divisional application of U.S. Ser. No. 08/582,668 filed Jan. 4, 1996 now abandoned.

BACKGROUND OF THE INVENTION

This invention relates to catalysts for hydrogenation and to hydrogenation reactions therewith. More particularly, this invention relates to noble metal Raney catalysts which can efficiently hydrogenate aromaticity-exhibiting ring portions and carbonyloxy portions of organic compounds and aromatic nitrile compounds and the like under conditions milder than conventional methods and to methods for the preparation of hydrogenated compounds with such catalysts.

DESCRIPTION OF RELATED ART

1) Hydrogenation Reaction of Aromaticity-exhibiting Ring Portions

There are many organic compounds which contain in their molecule rings which exhibit aromaticity. Hydrogenation reactions of such organic compounds generally are conducted under severe conditions, i.e., at high temperatures and at high hydrogen pressures.

Examples of prior art on catalysts for use in the hydrogenation of the aromaticity-exhibiting ring portions are described along with catalysts, compounds to be hydrogenated, and reaction conditions (reaction temperature and hydrogen pressure).

As the catalyst, there have been used Raney catalysts such as Raney Ni or Co, noble metal carried type catalysts such as Pd, Rh, Ru, etc. and base metal carried type catalysts. Reaction conditions therefor may depend on the natures of catalysts and compounds to be hydrogenated but generally comprise temperatures of 60 to 200° C. and pressures of 25–280 Kg/cm$^2$.

USSR Patent No. 706398 (1979) discloses hydrogenation of 4,4'-diaminodiphenylmethane into 4,4'-diaminodicyclohexyl-methane can be achieved under the conditions of a temperature of 60 to 140° C. and a hydrogen pressure of 40 to 130 atm. in the presence of skeleton Ru catalyst obtained by development of ruthenium-aluminum alloy with aqueous 20% sodium hydroxide solution.

As for the reaction conditions in concrete examples of the USSR patent, it was reported that 98.7% of 4,4'-diaminodicyclohexylmethane was obtained by 30 minute's reaction under severe conditions, i.e., a temperature of 140° C. and a hydrogen pressure of 120 atm. in isopropyl alcohol. However, only a brief description was made and no detailed explanation was given. In the experiments conducted by the present inventors, yield of 71.4% was obtained even after 4 hours, reaction. In the above mentioned prior art reference, there is recited only one species of 4,4'-diamino-diphenylmethane as a compound to be hydrogenated.

Japanese Patent Publication (Kokoku) No. 55-35177 (JP-B-55-035177) and Japanese Patent Publication (Kokai) (JP-A-02-258064) disclose that Raney ruthenium catalysts are effective as catalysts for ammonia synthesis. Japanese Patent Publication (Kokai) No. 5-253468 (JP-A-05-253468) discloses that Raney ruthenium catalysts are effective as catalysts for methanol synthesis. However, none of these references discloses effectiveness of the Raney ruthenium catalysts for hydrogenation reactions.

In contrast, by the use of the Raney ruthenium catalyst of the present invention described in detail hereinafter, ring portions of various aromatic compounds can be hydrogenated efficiently at a hydrogen pressure of 5 to 10 kg/cm$^2$, which is much lower than the condition described in the above-listed prior art references, at a temperature mostly around room temperature and at most about 100° C. None of the above publications can be said to be valid prior art which could render obvious to one skilled in the art the present invention directed to catalysts that allow hydrogenation of ring portions of a wide variety of aromatic compounds under mild conditions and to methods for the preparation of hydrogenated compounds with such catalysts.

TABLE

| Reference | Catalyst | Compound to be hydrogenated | Reaction Temperature (° C.) | Hydrogen Pressure (kg/cm$^2$G) |
| --- | --- | --- | --- | --- |
| JP-A-48-032845 | Co/CaO/Al2O3 | xylylene diamine | 130 | 200 |
| JP-B-51-007659 | Ru/carbon | xylylene diamine | 105 | 200 |
| JP-A-53-079840 | R/carbon | xylyiene diamine | 110 | 125 |
| JP-B-60-034526 | Ru/Al2O3 | 4-tert-butylphenol | 60–80 | 80 |
| JP-A-53-119855 | Ru/carbon | isopropylidene diphenol | 155 | 120 |
| JP-A-06-279339 | Ni/diatomaceous earth | bisphenol A (12 hours) | 200 | 25 |
| JP-A-42-001423 | Raney Ni | bisphenols | 200 | 80 |
| JP-A-45-035300 | carried type Rh | bisphenols | 75 | 50 |
| JP-A-06-009461 | Ru/carbon | bisphenols | 140 | 50 |
| JP-A-06-279368 | Ru/Al2O3 | aromatic dinitrile | 140 | 150 |
| JP-A-06-306019 | Ru/Co/Al2O3 | methylene diamine | 180 | 58 |
| JP-A-56-012348 | Raney Ni | carbomethoxybenzaldehyde oxime | 150 | 90 |
| JP-A-04-018935 | CO oxide/carried Rh | phenylene diamine | 165 | 5 |
| JP-A-04-247056 | Ru/Co/Mn Al2O3 | bis(4-aminophenyl)methane | 140 | 260 |
| JP-A-63-295533 | Ru/carbon | pyridine | 160 | 80 |
| JP-A-03-002162 | Ru/carbon | picolic acid | 80–160 | 30–50 |
| JP-A-58-108439 | Pd/Ru/carbon | terephthalic acid | 150 | 100 |

2) Hydrogenation of carboxylic acids and their esters

Many methods have been known in which compounds having a carbonyloxy group (—CO—O—) are reacted with hydrogen to produce corresponding alcohols or the like.

For example, as a method for hydrogenating carboxylic acids, a method using a rhenium oxide catalyst is disclosed in J. Org. Chem. 24, 1847 (1959). This method involves a reaction which must be carried out for a long time at high pressures and whose product contains many by-products.

Use of cobalt-yttrium-palladium catalysts in hydrogenation of lauric acid into lauryl alcohol is known (Japanese Patent Publication (Kokoku) No. 4-36140 (JP-B-04-036140)). However, the method uses severe reaction conditions, i.e., a temperature of 225° C. and a hydrogen pressure of 250 kg/cm$^2$.

As methods of hydrogenation of carboxylic acid esters, there have been known a method in which the ester group of a cyclohexane dicarboxylic ester is hydrogenated with a copper-chromium catalyst at a reaction temperature of 220° C. at a reaction pressure of 150 kg/cm$^2$ as disclosed in Japanese Patent Publication (Kokai) No. 52-242 (JP-A-52-000242), a method in which the benzene skeleton of dimethyl terephthalate is hydrogenated, followed by hydrogenation of the ester portion of the product with a copper-chromium catalyst ($CuO-Cr_2O_3-BaO$) at a reaction temperature of 120–220° C. at a reaction pressure of 300 Bar as disclosed in U.S. Pat. No. 5,030,771, and so on. These reactions each must be carried out under severe conditions.

Further, there is known a method in which a catalyst containing ruthenium and tin carried on titania is used for hydrogenating dimethyl 1,4-cyclohexanedicarboxylate at a temperature of 270–280° C. at a pressure of 90–100 kg/cm$^2$ to obtain 1,4-cyclohexanedimethanol as disclosed in Japanese Patent Publication (Kokai) No. 6-228028. The reaction conditions used in this method is also severe. Also, there is known a method in which a catalyst containing ruthenium and tin carried on titania is used for hydrogenating dimethyl dimerate at a temperature of 250° C. at a pressure of 100 kg/cm$^2$ into an alcohol as disclosed in Japanese Patent Publication (Kokai) No. 6-228027. Also, the reaction conditions used are severe and unsatisfactory.

Many prior art references have been known on the use of Raney catalysts as a catalyst for the hydrogenation of compounds having a carbonyloxy group. For example, there are known use of Raney nickel, Raney rhenium, and Raney copper catalysts (Japanese Patent Publication (Kokai) No. 5-345735), use of Raney nickel catalyst (Japanese Patent Publication (Kokai) No. 55-40685), and so on.

As examples of use of noble metal catalysts, there are disclosed hydrogenation reactions in the presence of compound (alloy) catalysts comprising at least one noble metal selected from noble metal elements belonging to the period 5 or 6 in the groups VIII, IX, and X and an alloy of such noble metal with other metal(s) (Japanese Patent Publication (Kohyo) Nos. 1-503459 and 3-500657).

However, the former Raney catalysts do not suggest the noble metal Raney catalysts. In addition, the latter noble metal-other metal alloy. catalysts are carried type catalysts. In either of the cases, a problem arises in that high reaction temperatures and high reaction pressures are used.

Catalyst systems thus far known need severe reaction conditions such as high temperatures and high pressures as described above and show low conversion or low selection and, hence, there is a keen need for development of a method which can efficiently produce alcohols or the like from carbonyloxy group-containing compounds.

Also, a method is needed which can efficiently perform hydrogenation of the rings and the carbonyloxy groups simultaneously in one step in hydrogenation reaction of aromatic compounds having a carbonyloxy group.

3) Hydrogenation of aromatic nitrile compounds

In the case where rings and nitrile groups of aromatic nitrile compounds are hydrogenated simultaneously, catalysts which are suitable for hydrogenating the aromatic rings are not necessarily the same as catalysts which are suitable for hydrogenating nitrile groups. Accordingly, in industrial applications, different catalysts must be used in the nitrile group hydrogenation step and aromatic ring hydrogenation step so that so-called two-step reactions are adopted. Therefore, development of a suitable catalyst is desired which can hydrogenate both nitrile groups and aromatic rings simultaneously, and there is desired a method in which aromatic nitrile compounds are hydrogenated in a one-step reaction which is advantageous industrially.

As examples of one-step hydrogenation reactions for rings and cyano groups, there have been known methods in which isophthalonitrile or terephthalonitrile are hydrogenated with a carried type rhodium catalyst in the presence of ammonia at a hydrogen pressure of 35–140 kg/cm$^2$ to produce 1,3- or 1,4-bis(aminomethyl)cyclohexane as disclosed in Japanese Patent Publication (Kokai) No. 51-68540, aromatic dinitriles are hydrogenated with carried type ruthenium catalysts in the presence of ammonia at a pressure of 50–150 atm. to produce bis(aminomethyl)cyclohexane as disclosed in Japanese Patent Publication (Kokai) No. 6-27936, a catalyst containing ruthenium and palladium carried on an oxide carrier is used in the presence of ammonia at a hydrogen pressure of 750 psi or higher to hydrogenate terephthalonitrile to produce 1,4-bis(aminomethyl)-cyclohexane as proposed in U.S. Pat. No. 4,070,399.

However, these methods are cumbersome to operate since they need presence of excess liquid ammonia at the time of hydrogenation reaction and relatively high pressures such as 35 kg/cm$^2$ or higher, and need recovery of ammonia when employed onlan industrial scale.

As described above, upon hydrogenating the ring portions that exhibit aromaticity of aromatic compounds, carbonyloxy portions (carboxylic acids and esters), and ring portions and at the same time carbonyloxy groups or nitrile groups, the conventional reaction conditions are disadvantageous since in most cases high temperatures and high hydrogen pressures are necessary and, particularly, extremely long reaction times are needed when low hydrogen pressures are used. When hydrogen reactions are carried out on an industrial scale, among reaction conditions, some conditions, particularly hydrogen pressure, are very important factors upon designing reaction installment.

However, the conventional hydrogenation catalysts are disadvantageous from practical viewpoints since they need usually high hydrogen pressures and relatively high temperatures for hydrogenation, so that development of catalysts which can catalyze hydrogenation reactions at low temperatures and low hydrogen pressures.

Therefore, an object of this invention is to provide a catalyst which can proceed hydrogenation of organic compounds having in their molecule aromaticity-exhibiting ring portions at low temperatures and at low hydrogen pressures.

Another object of this invention is to provide a method for preparing compounds having hydrogenated ring portions derived from aromaticity-exhibiting ring portions with such a catalyst.

Still another object of this invention is to provide a catalyst which can efficiently hydrogenate compounds having a carbonyloxy group in their molecule into corresponding alcohols or the like at high conversion and selection under reaction temperature and reaction pressure conditions milder than the conventional methods.

Yet another objection of this invention is to provide a method for preparing alcohols or the like from compounds having a carbonyloxy group with such a catalyst.

Further, an object of this invention is to provide a catalyst which can hydrogenate organic compounds having in their molecule a carbonyloxy group and a ring portion exhibiting aromaticity such that only the ring portion is selectively hydrogenated or both the ring portion and the carbonyloxy group are hydrogenated.

Another object of this invention is to provide a method for preparing selectively hydrogenated or completely hydrogenated compound with such a catalyst.

A further object of this invention is to provide a catalyst which can hydrogenate the aromatic ring and nitrile group of an aromatic nitrile compound simultaneously in one step at relatively low hydrogen pressures without ammonia.

A still further object of this invention is to provide a method for preparing cyclic methylamine (aminomethyl compound) whose aromatic ring is hydrogenated from an aromatic nitrile compound with such a catalyst.

SUMMARY OF THE INVENTION

This invention relates to the following hydrogenation catalysts and methods for preparing hydrogenated compounds:

1) Noble metal Raney catalyst for hydrogenation;
2) Noble metal Raney catalyst of 1) above for hydrogenating a ring portion contained in the molecule that exhibits aromaticity;
3) Noble metal Raney catalyst of 1) above for hydrogenating a carbonyloxy (—CO—O—) group in the molecule;
4) Noble metal catalyst for simultaneously hydrogenating a ring portion exhibiting aromaticity and a carbonyloxy group contained in the molecule;
5) Noble metal Raney catalyst for simultaneously hydrogenating a ring portion exhibiting aromaticity and a nitrile group contained in the molecule;
6) Noble metal Raney catalyst of 1) above, in which the catalyst is a modified catalyst that comprises one or more other metal elements in addition to the noble metal.
7) Noble metal Raney catalyst of 1) above, in which the noble metal is ruthenium;
8) Noble metal Raney catalyst of 6) above, in which the one or more other metals are selected from the group consisting of chromium, manganese, tin, cobalt, iron, nickel, rhenium, silicon, zinc, silver, boron, vanadium, lead, indium, niobium, gold, molybdenum, tungsten, scandium, titanium, antimony, and lanthanum;
9) Method for preparing a compound whose aromaticity-exhibiting ring portion in the molecule is hydrogenated, in which a noble metal Raney catalyst is used as a catalyst.
10) Method for preparing alcohol, lactone, or ether, in which a compound having a carbonyloxy group in the molecule is reacted with hydrogen in the presence of a noble metal Raney catalyst to reduce the carbonyloxy group into a methyleneoxy (—CH$_2$—O—) group;
11) Method for preparing an alcohol compound whose aromatic ring and carboxylic acid or carboxylate group are both hydrogenated, in which an aromatic carboxylic acid or carboxylate is reacted with hydrogen in the presence of a noble metal Raney catalyst;
12) Method for preparing an aminomethyl compound whose aromatic ring and nitrile group are both hydrogenated, in which an aromatic nitrile compound is reacted with hydrogen in the presence of a noble metal Raney catalyst;
13) Method of 9) above, in which the noble metal Raney catalyst comprises Raney ruthenium;
14) Method of 9) above, in which the noble metal Raney catalyst comprises a modified Raney ruthenium catalyst;
15) Method of 9) above, in which the noble metal Raney catalyst comprises a Raney ruthenium and a modified Raney ruthenium catalyst;
16) Method for preparing a compound whose aromaticity-exhibiting ring portion is hydrogenated according to 9) above, in which an aromatic compound or its derivative is reacted with hydrogen in the presence of a Raney ruthenium catalyst at 5 to 30 kg/cm$^2$ at a temperature of room temperature to 130° C.

DETAILED DESCRIPTION OF THE INVENTION

Hereinafter, this invention will be described in greater detail.

The noble metal Raney catalysts used in this invention include noble metal catalysts obtained by producing alloys of acid- or alkali-soluble metals such as aluminum, silicon, zinc, magnesium, etc. with alkali- or acid-insoluble noble metals are prepared and then eluting the alkali- or acid-soluble metals from the alloys.

More specifically, Raney ruthenium, Raney rhodium, Raney palladium, Raney osmium, Raney iridium, Raney platinum, and their modifications (modified noble metal Raney catalysts). Particularly preferred are Raney ruthenium catalysts.

Modified Raney catalysts as used herein refer to catalysts which comprise one of the above-described noble metal Raney catalyst and one or more other elements, more specifically, noble metal Raney catalyst which contain one or more elements belonging to the 3rd to 15th groups in the periodic table. Examples of such additional elements include chromium, manganese, tin, cobalt, iron, nickel, rhenium, silicon, zinc, silver, boron, vanadium, lead, indium, niobium, gold, molybdenum, tungsten, scandium, titanium antimony, lanthanum, etc.

In this invention, noble metal Raney catalysts and modified noble metal Raney catalysts can be used in combination with each other.

Here, a general method for preparing the noble metal Raney catalysts will be described taking Raney ruthenium as an example. Noble metal Raney catalysts other than Raney ruthenium (hereafter, sometimes abbreviated as "R-Ru") can be prepared similarly.,.

For Raney catalysts, usually Al is used as the alkali- or acid-soluble metal. This is not only because Al is most cheap and is economically advantageous but also because Al is easy to process and handle as well as highly safe. In the case of R-Ru catalysts, Al is usually used for the same reason but the alkali- or acid-soluble metal which can be used is not limited thereto.

R-Ru catalysts are prepared by the following method. First, when the alkali- or acid-soluble metal is Al, for example, Ru or Ru and one or more other metals is or are molten into 15–90% by weight of Al to produce an alloy mainly composed of Al and Ru (hereafter, abbreviated as "R-Ru alloy"). The R-Ru alloy thus obtained is then ground so as to have a suitable particle size or molten R-Ru alloy is quenched and solidified by gas atomizing to obtain fine particles. The fine particles are developed with alkali or acid.

Suitable composition of R-Ru alloy comprises 10–85% by weight of Ru and 90–15% by weight of Al, and preferably a composition of about 50% by weight of Ru and about 50% by weight can be used advantageously. For preparing the R-Ru alloy, Ru and Al powders are mixed and pressure molded to form pellets, which are then sintered or molten at high temperatures. The pellets can be molten easily in an arc melting furnace under inert gas stream (e.g., argon, helium gas, etc.) to produce R-Ru alloy. Usually, the R-Ru alloy must be divided into fine particles before development. As the dividing method, there can be used a mechanical pulverization method, a gas atomizing method, and the like.

As the fine particles of R-Ru alloy which can be used in the methods of the invention, there can be used advantageously those fine particles produced by "high frequency induction melting gas atomizing method" exemplified in Industrial Rare Metals No. 108, page 31 (1994), those fine particles obtained by atomizing molten alloy in an inert gas.

R-Ru alloy fine particles obtained by grinding or the like can be developed by suspending them in an aqueous caustic alkali solution. As the caustic alkali, there can be used metal hydroxides such as hydroxides of Li, Na, K, Rb, Cs, etc. Of these, sodium hydroxide or potassium hydroxide may be used preferably. Further, sodium hydroxide can be used advantageously from economical viewpoints.

The amount of the caustic alkali to be used is determined taking into consideration the amount of Al in the R-Ru alloy, and the concentration of caustic alkali is preferably in the range of 2 to 40% by weight, and the developing temperature is in the range of room temperature to 120° C.

The developing time may vary depending on the amount of Al in the R-Ru alloy, particle size of the crushed alloy, concentration of caustic alkali and the like but usually it is advantageous to develop for 1 hour or longer.

After the development, the catalyst is washed with water so that the caustic alkali in the catalyst can be removed as much as possible. In this manner, fine particles of R-Ru catalyst can be obtained.

In industrial applications, the R-Ru catalysts can be prepared, for example, by the following procedure:
1) Preparation and crushing of R-Ru alloy Al and Ru are molten in a weight proportion of 50/50 to produce an alloy. The alloy ingot is crushed and fine particles of the alloy that pass 100 mesh are recovered.
2) Developing An aqueous 10–35% by weight sodium hydroxide solution is charged in a developer tank and retained at 90° C. while stirring. The above-described alloy powder is charged so that the temperature inside the developer tank can be kept at 90 to 95° C. with removing heat by use of a cooling coil equipped with the developer. After the total amount of the alloy powder is charged, the temperature inside the tank is kept to 90° C. for a certain period of time for aging before the development is completed. The development involves generation of hydrogen and is a vigorous exothermic reaction and, hence, control of temperature is important.
3) Washing with Water After the development, the reaction mixture is left to stand so that the developed catalyst can precipitate sufficiently and then the supernatant is decanted. Thereafter, deionized water deoxygenated in advance is added to the residue and the mixture is stirred at room temperature, followed by leaving the mixture to stand. This gradient washing step is repeated 5 to 10 times. Finally, the supernatant is discarded to obtain a developed catalyst dipped in water.

When the R-Ru catalyst according to an example of this invention is used in hydrogenation reactions, it shows high activity particularly at low temperatures and at low hydrogen pressures. The reason for this is not clear. However, taking into consideration how the Raney catalysts are produced, the high activity is supposed to be attributable to high density of active sites derived from Ru metal.

Raney Ni catalysts are well known as a hydrogenation catalyst for intramolecular aromatic moieties, and modified Raney nickel catalysts obtained by addition of a small amount of Ru to the Raney Ni catalysts are also disclosed in the prior art references.

In the references, there are disclosed the following compounds as examples of the compounds to be hydrogenated.
(1) Nitrophenol (Izv. Akad. Nauk SSSR, Scr. Khim., Vol. 17 (No. 4), pages 49–58 (1967);
(2) Nitrophenol (Ktol. Vosstanv. Gidrirov. Zhidk, Faze, pages 80–84 (1970);
(3) Heterocyclic amines, aromatic amines, aromatic carboxylic acids (Issled. Obla. Getero tsikil. Soedin., pages 5–14 (1971);
(4) Phenol (Zh. Prikl. Khim. (Leningrad), Vol. 46 (No. 12), pages 2707–2711 (1973));
(5) Nitrobenzenes, hydroxynitrobenzens (Zh. Obsch. Khim., Vol. 48 (No. 2), pages 385–390 (1978));

The R-Ru catalysts differ from the Ru-modified Raney Ni catalysts in the following points and are not suggested by the above-described prior art references.
i) The catalysts of this invention are R-Ru catalysts and active sites effective for hydrogenation are supposed to be in the form of metallic Ru. However, in the modified Raney Ni catalysts, the active sites effective for hydrogenation are considered to be in the form of metallic Ni. Although it is unclear how the added Ru is combined, the Ru added plays a role of increasing the function of Ni as by coordinating with metallic Ni.
ii) Reportedly, the amount of Ru added to Raney Ni is within the range of 0.01 to 20% by weight. However, in the case of R-Ru catalysts, the amount of Ru is preferably at least 50% by weight, and more preferably at least 70% by weight.

As described above, as a catalyst for hydrogenating an aromatic portion in the molecule, it is known to use one comprising Raney Ni and a small amount of Ru. However, as already stated in the part of Description of Related Art above, only one example of reduction of 4,4'-diaminodiphenylmethane into 4,4'-diaminodicyclohexylmethane is disclosed in USSR Patent 706398 (1979) so far as the R-Ru catalysts are concerned. According to the disclosure of the USSR patent, reaction is carried out under severe conditions, i.e., at a temperature of 140° C. and at a hydrogen pressure of 120 atm. It is not disclosed in the USSR patent that the rings of various aromatic compounds can be hydrogenated under conditions by far milder and further that carbonyloxy group or the nitrile group and the ring in a nitrile group-containing aromatic compound can be hydrogenated efficiently as in this invention.

As described above, none of the prior art shows the advantageous effects of this invention.

Modified noble metal Raney catalysts

Modified noble metal Raney catalysts used in this invention can be prepared by one of the following two methods, i.e., alloying method and addition method.

Upon preparing noble metal Raney alloy, the alloying method simultaneously adds one or more other metals for modification in addition to major noble metal element to obtain alloys. The amount of the other metal(s) is not limited particularly but generally is within the range of 0.1 to 50% by weight, preferably 5 to 30% by weight of the major noble metal element.

On the other hand, the one or more other metal elements may be added upon development of the noble metal Raney alloy with an alkali or acid by adding an alkali- or acid-soluble metal salt as a modifier so that the metal salt can coexist, or after the alloy is developed with an alkali or acid by the modifier metal salt. It is also possible to add the modifier metal salt during hydrogenation reaction. 1) Hydrogenation of compounds having an aromaticity-exhibiting ring portion in the molecule Examples of the compounds having an aromaticity-exhibiting portion in the molecule that are objective compounds for hydrogenation by this invention include benzene and its derivatives, pyridine and its derivatives, pyridazine and its derivatives, pyrimidine and its derivatives, pyrazine and its derivatives, triazine and its derivatives, naphthalene and its derivatives, azulene, quinoline and its derivatives, isoquinoline and its derivatives, quinoxaline and its derivatives, phthalazine and its derivatives, quinazoline and its derivatives, cinnoline and its derivatives, pteridine and its derivatives, and the like.

The derivatives described above are not limited particularly but include compounds substituted directly or indirectly by electron attracting groups such as —COOH and/or electron donating groups such as —OH and —NH$_2$.

Further, examples of the compounds having an aromaticity-exhibiting ring portion in the molecule which are hydrogenated by this invention include the following compounds: benzene, toluene, xylene, mesitylene, ethylbenzene, diphenylmethane, tetraline, styrene, allylbenzene, 1,2-dihydronaphthalene, stilbene, biphenyl, chlorobenzene, benzyl chloride, fluorobiphenyl, anisole, β-methoxystyrene, allyl phenyl ether, diphenyl ether, benzyl ether, methoxybiphenyl, styrene oxide, phthalan, 2,3-dihydrobenzofuran, xanthene, 2-phenyl-1,3-dioxolane, 1,3-benzodioxole, trimethylisobenzoate, phenol, cathecol, resorcinol, hydroquinone, phenoxyphenol, phenylphenol, 4,4'-biphenol, 4,4'-biphenol ethylene oxide adduct, 4,4'-biphenol propylene oxide adduct, bis(4-hydroxyphenyl)methane, bisphenol A, bis(4-hydroxyphenyl)methane ethylene oxide adduct, bis(4-hydroxyphenyl)methane propylene oxide adduct, bisphenol A ethylene oxide adduct, bisphenol A propylene oxide adduct, benzyl alcohol, benzenedimethanol, phenoxybenzyl alcohol, biphenylmethanol, stilbenemethanol, 1,5-dihydroxy-1,2,3,4-tetrahydronaphthalene, 4-chromanol, 9-hydroxyfluorene, cinnamyl alcohol, hydroxybenzoic acid, 4'-hydroxy-4-biphenylcarboxylic acid, biphenyldimethanol, aniline, 1-phenylpiperidine, 2-aminoethanol, 4,4'-methylenedianiline, 4,4'-methylenedianiline ethylene oxide adduct, 4,4'-methylenedianiline propylene oxide adduct, phenylenediamine, phenylenediamine, phenylenediamine ethylene oxide adduct, phenylenediamine propylene oxide adduct, aminobiphenyl, benzylaniline, phenoxyaniline, benzylamine, aminophenylmethane, xylylenediamine, xylylenediamine ethylene oxide adduct, xylylenediamine propylene oxide adduct, aminobenzylamine, indoline, nitrosobenzene, nitorosobenzene, dinitrobiphenyl, 1,3-diphenylacetone, tetralone, acetophenone, deoxybenzoin, 4-acetylbiphenyl, benzophenone, anthrone, 4-chromanone, phenylacetaldehyde, veratrol, benzaldehyde, piperonal, phenylacetic acid, mandelic acid, 4-biphenylacetic acid, benzoic acid, phthalic acid, isophthalic acid, terephthalic acid, biphenyltetracarboxylic acid, 4,4'-biphenyldicarboxylic acid, 1,4-phenylenediacetic acid, phenylglyoxylic acid, phenylglycine, N-phenylglycine, 4-hydroxyphenylglycine, triptophane, benzyl acetate, methylphenyl acetate, methyl benzoate, 4,4'-oxybis(methylbenzoate), dimethyl phthalate, dimethyl isophthalate, dimethyl terephthalate, phenyl acetate, hydroquinone acetate, diallyl terephthalate, 2-coumaranone, γ-phenyl-γ-butyrolactone, benzoic anhydride, phtalic anhydride, biphenyltetracarboxylic anhydride, phenylacetyl chloride, bonzoyl chloride, phthaloyl dichloride, isophthaloyl dichloride, terephthaloyl dichloride, acetoanilide, benzamide, phenylurea, benzylurea, phenyl carbamate, benzyl carbamate, 1-phenyl-2-pyrrolidinone, oxyindole, phthalimide, 2-phenyl-2-oxazoline, 5-methyl-5-phenylhydantoin, benzyl cyanide, 1,4-phenylenediaceto-nitrile, benzoyl acetonitrile, benzonitrile, phthalonitrile, isophthalonitrile, terephthalonitrile, 4-biphenylcarbonitrile, tolunitrile, phenyl isocyanate, benzyl isocyanate, phenylenedibenzyl isocyanate, phenylphosphine, triphenylphosphine, phehnylphosphinic acid, triphenyl phosphate, triphenyl phosphite, pyridine, dipyridyl, picoline, vinylpyridine, lutidine, phenylpyridine, benzylpyridine, methylethylpyridine, methylvinylpyridine, 2,3-cyclohexenopyridine, chlorofluoropyridine, methoxypyridine, pyridylcarbinol, hydroxypyridine, aminopyridine, aminomethylpyridine, acetylpyridine, benzoylpyridine, di-2-pyridylketone, pyridinecarboxaldehyde, picolic acid, nicotinic acid, pyridylacetic acid, ethyl picolate, methyl nicotinate, methyl isonicotinate, 3-acetoxypyridine, nicotinic hydrazide, 2,3-pyridinedicarboxylic anhydride, nicotinamide, isonicotinamide, 3,4-pyridinedicarboximide, methyl-3-pyridyl carbamate, 1-(3-pyridylmethyl)urea, cyanopyridine, pyrdylacetonitrile, pyridinesulfonic acid, pyridazine, methylpyridazine, 3,6-dichloropyridazine, 3,6-dihydropyridazine, pyrimidazine, pyrimidine, 4-methylpyrimidine, 4-phenylpyrimidine, 2-chloropyrimidine, 2-hydroxypyrimidine, 2-aminopyrimidine, pyrazine, methylpyrazine, chloropyrazine, methoxypyrazine, aminopyrazine, acetylpyrazine, pyrazinecarboxylic acid, pyrazineamide, 1,3,5-trizaine, cyanuric chloride, cyanuric acid, melamine, naphthalene, methylnaphthalene, phenylnaphthalene, chloronaphthalene, chloromethylnaphthalene, methoxynaphthalene, naphthol, 1,5-dihydroxynaphthalene, naphthalenemethanol, aminonaphthalene, 1,5-diaminonaphthalene, naphthalenemethylamine, nitronaphthalene, 1,5-dinitronaphthalene, acetonaphthalene, naphthoaldehyde, naphthylacetic acid, naphthoic acid, 2,6-naphthalenedicarboxylic acid, 2,5-naphthalenedicarboxylic acid, 1,4-naphthalenedicarboxylic acid, methyl naphthaleneacetate, naphthyl acetate, dimethyl 2,6-naphthalenedicarboxylate, 2,6-dihydroxynaphthalene, naphthaleneacetamide, 2,6-diisopropylnaphthalene, diaminonaphthalene, naphthylacetonitrile, naphthyl iocyanate, naphthalenesulfonic acid, quinoline, methylquinoline, chlorq.quinoline, methoxyquinoline, hydorxyquinoline, aminoquinoline, nitroquinoline, quinolinecarboxaldehyde, quinolinecarboxylic acid, quinolinecarbonitrile, isoquinoline, methylisoquinoline, hydroxyisoquinoline, aminoisoquinoline, nitroisoquinoline, isoquinolinecarboxylic acid, methyl isoquinolinecarboxylate, isoquinolinecarbonitrile, isoquinolinesulfonic acid, quinoxaline, methylquinoxaline, quinoxalinol, ethyl quinoxalinecarboxylate, quinoxalinecarboxylic acid, quinoxaloyl chloride, 2,3-dichloroquinoxaline, phthalazine, 1,4-dichlorophthalazine, quinazoline, hydroxyquinazoline, cinnoline, cinnolinecarboxylic acid, anthracene, acridine, phenathroline, and the like.

Hydrogenation reaction of such compounds having an aromaticity-exhibiting ring portion in the molecule can be carried out by contacting the starting compound with hydrogen in the presence of the noble metal Raney catalyst of this invention. The reaction can proceed either in a liquid phase or in a gaseous phase. The liquid phase hydrogenation method is used advantageously.

In the case where the hydrogenation reaction is. practiced in a liquid phase, the reaction may proceed using the compounds to be hydrogenated without dilution with a solvent when they are liquid or molten at room temperature or higher temperatures, which is also advantageous from economical viewpoints. However, taking into consideration removal of reaction heat, separation and purification of products, and so on, usually the method in which the compounds to be hydrogenated are diluted with a solvent is preferred.

Preferred examples of the solvent used in the method of this invention include the following: alcohol solvents, e.g., methanol, ethanol, n-propanol, isopropanol, n-butanol, isobutanol, secondary butanol, tertiary butanol, n-amyl alcohol, isoamyl alcohol, secondary or tertiary amyl alcohol, 3-pentanol, n-hexanol, methylamyl alcohol, 2-ethylbutanol, n-heptanol, 2-heptanol, 3-heptanol, n-octanol, 2-octanol, 2-ethylhexanol, nonanol, n-decanol, cyclohexanol, 2-methylhexanol, and the like, polyhydric alcohol solvents such as ethylene glycol, ethylene glycol monomethyl ether, ethylene glycol dimethyl ether, ethylene glycol monoethyl ether, ethylene glycol diethyl ether, ethylene glycol isopropyl ether, ethylene glycol monobutyl ether, ethylene glycol dibutyl ether, ethylene glycol monohexyl ether, methoxymethoxyethanol, diethylene glycol, diethylene glycol monomethyl ether, diethylene glycol monobutyl ether, diethylene glycol dimethyl ether, and the like.

Examples of aliphatic and alicyclic hydrocarbon ether solvents include ethyl ether, n-propyl ether, isopropyl ether, n-butyl ether, acetyl ether, diisoacyl ether, n-hexyl ether, tetrahydrofuran, dioxane, dicyclohexyl ether, and the like.

As saturated aliphatic and alicyclic hydrocarbon solvents, there can be suitably used pentane, hexane, heptane, octane, decane, cyclohexane, methylcyclohexane, cyclooctane, and the like.

When the compounds to be hydrogenated and the resulting hydrogenated compounds are soluble in water, water may be used as a solvent. If the compounds to be hydrogenated are sparingly soluble in water, water which coexists in the reaction mixture acts as a cocatalyst and addition of a suitable amount of water in the reaction mixture which is water-insoluble is sometimes advantageous in increasing the performance of the catalyst.

The solvents can be used singly or it is possible to use them as a mixed solvent.

Addition of alkali metal salts, e.g., hydroxides of metals such as Li, Na, K, and the like sometimes increases the solubility of the compounds to be hydrogenated in solvents or increases hydrogenation reaction rate. Sometimes preferred solvents exist depending on the kind of the compounds to be hydrogenated so that it is advantageous to choose solvents suitable for respective compounds to be hydrogenated.

The method of hydrogenating an aromaticity-exhibiting ring portion (hydrocarbon ring) in a compound with the noble metal Raney catalyst of this invention will be described in detail below.

The catalyst may be used in the form of powder as a suspension bed or in the form of granules as a fixed bed. The type of reaction may be of a continuous type or of a batch type. when the reaction is performed on an industrial scale, it is practically advantageous suspend the noble metal Raney catalyst in a reactor of the type of fluid agitator and conduct hydrogenation reaction continuously.

The catalyst is used usually in amounts of 0.01 to 50% by weight, preferably 0.02 to 25% by weight, expressed as a concentration in the reaction mixture. The noble metal Raney catalyst of this invention can be as is after the development of the alloy or may be subject to an appropriate activation treatment such as reduction treatment before use.

It is desirable that the noble metal Raney catalysts of this invention be prevented from contacting oxygen gas or oxygen-containing gases before use and during use so that the catalysts can fully exhibit their original, uninhibited catalytic activities to attain good reaction results.

The reaction temperature is within the range of 0 to 300° C., preferably 10 to 200° C., and more preferably room temperature to 150° C. Below 00° C., sufficient hydrogenation rate cannot be obtained. At temperatures above 300° C., no significant increase in the performance is obtained and use of such high temperatures is noneconomical.

The reaction pressure is within the range of 1 to 200 kg/cm$^2$, preferably 2 to 100 kg/cm$^2$, and more preferably 5 to 50 kg/cm$^2$ as a partial pressure of hydrogen. At a hydrogen pressure of below 1 kg/cm$^2$, no sufficient hydrogenation rate can be obtained whereas use of a hydrogen pressure of above 200 kg/cm$^2$ results in no significant increase in the performance of the catalyst and, hence, is noneconomical.

With the noble metal Raney catalysts, hydrogenation reaction of the aromaticity-exhibiting ring portion in the molecule proceeds at sufficient rate even at low hydrogen pressures within the range of 5 to 10 kg/cm$^2$, and no high pressure installation is needed as a practical hydrogenation installment so that this invention is much more advantageous economically.

Hydrogen gas used in this invention does not have to be highly pure but may contain inert gases such as nitrogen, carbon dioxide, methane, etc. which do not affect the hydrogenation reaction. Reducing agents such as LiAlH$_4$, NaBH$_4$, hydrazine, etc. may coexist as a hydrogen gas source in the reaction system.

The reaction may be carried out without solvents or in solvents. When solvents are used, the amount of the solvent is within the range of 1 to 30 times by weight, preferably 3 to 10 times by weight based on the weight of the compounds to be hydrogenated.

2) Hydrogenation of compounds having oxycarbonyl group

Among the compounds having an oxycarbonyl group, i.e., compounds to be hydrogenated by this invention, carboxylic acids may be monocarboxylic acids or polycarboxylic acids.

As the monocarboxylic acids, there can be used any one of aliphatic carboxylic acids, aromatic carboxylic acids, aromatic-aliphatic carboxylic acids, and alicyclic carboxylic acids. The polycarboxylic acids include aliphatic polycarboxylic acids, alicyclic polycarboxylic acids, and aromatic polycarboxylic acids.

Aromatic carboxylic acid esters may be aliphatic alcohol esters of the above-described carboxylic acids and carboxylic anhydride may be anhydrides corresponding to the above-described carboxylic acids.

More specifically, examples of the aliphatic carboxylic acids include acetic acid, propionic acid, butyric acid, capronic acid, caprylic acid, pivalic acid, capric acid, lauric acid, stearic acid, isobutyric acid, etc.; examples of polycarboxylic acids include oxalic acid, malonic acid, maleic acid, succinic acid, glutaric acid, adipic acid, etc.; examples of aliphatic carboxylic acids include aliphatic carboxylic acids such as crotonic acid, etc.; examples of aromatic polycarboxylic acids include benzoic acid, o-chlorobenzoic acid, m-chlorobenzoic acid, p-chlorobenzoic acid, m-fluorobenzoic acid, p-fluorobenzoic acid, toluylic acid, m-hydroxybenzoic acid, p-hydroxybenzoic acid, phthalic acid, terephthalic acid, isophthalic acid, naphthalenedicarboxylic acid, phenoxybenzoic acid, etc.; examples of the alicyclic carboxylic acids include cyclohexanedicarboxylic acid, etc. However, this invention is not limited thereto.

As the carboxylic acid esters, there can be used lower alcohol esters, such as methyl ester, ethyl ester, and propyl ester, as well as higher alcohol esters, such as lauryl alcohol ester, of the above-described carboxylic acids. Also, there can be cited polyhydric alcohol esters, such as ethylene glycol, propylene glycol, and glycerol, of the above-described carboxylic acids. Furthermore, cyclic esters, such as γ-butyrolactone and ε-caprolactone, of the above-described carboxylic acids can also be used.

As the carboxylic anhydrides, there can be cited anhydrides corresponding to the above-described carboxylic acids, such as maleic anhydride, succinic anhydride, phthalic anhydride, and the like. However, other anhydrides of the above-described carboxylic acids may also be used.

The hydrogen pressure in the hydrogenation reaction may be usually 1 to 200 kg/cm$^2$, preferably 5 to 100 kg/cm$^2$. Suitable reaction temperature is within the range of room temperature to 300° C., preferably 40 to 250° C., and more preferably 50 to 180° C. The reaction time may vary widely depending on the reaction conditions, the reactivity of the compounds having an oxycarbonyl group but is a sufficient time for completing the reaction, which is usually within the range of about 1 to about 24 hours.

The amount of the catalyst used in the reaction is desirably within the range of 0.1 to 100 parts by weight based on 100 parts by weight of the starting material for the reaction. However, the amount of the catalyst may be selected freely as far as practically acceptable reaction rate can be obtained depending on various conditions including the reaction temperature and hydrogen pressure.

The type of reaction may be of a liquid phase suspension bed type or of a liquid phase fixed bed type, or of a gas phase reaction. In the case where the hydrogenation reaction is practiced in a liquid phase, the reaction may proceed using the compounds to be hydrogenated without dilution with a solvent when they are liquid or molten at room temperature or higher temperatures, which is also advantageous from economical viewpoints. However, taking into consideration removal of reaction heat, separation and purification of products, and so on, usually the method in which the compounds to be hydrogenated are diluted with a solvent is preferred. The solvent is not limited particularly and any solvent that is usually used as a solvent in reduction reactions may be used as far it can dissolve the starting materials. Specific examples of such solvents include dioxane, tetrahydrofuran, cyclohexane, methanol, ethanol, n-propanol, isopropanol, n-butanol, cyclohexanol, ethylene glycol, 1,4-butanediol, 1,6-hexanediol, ethylene glycol methyl ether, ethylene glycol ethyl ether, ethylene glycol dimethyl ether, diethylene glycol diethyl ether, triethylene glycol methyl ether, triethylene glycol ethyl ether, triethylene glycol dimethyl ether, triethylene glycol diethyl ether, cyclohexanedimethanol, and the like.

As a preferred example, when the compounds to be hydrogenated or the resulting products are water-soluble, a preferred solvent is a water containing organic solvent or water. Generally, organic solvents containing appropriate amounts water or water itself are used alone as the solvent, hydrogenation rates and selectivities increase.

Hydrogenation of compounds having an oxycarbonyl group by the method of this invention can be classified into several reaction types depending on the kind of the oxycarbonyl group, as below:

(A) Generation of a corresponding alcohol from the carboxylic acid;

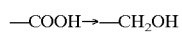

(B) Generation of a cyclic ether and a diol from the lactone;

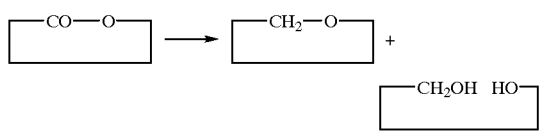

(C) Generation of an alcohol from the carboxylic acid ester;

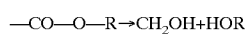

(D) Generation of an alcohol form the acyclic carboxylic anhydride;

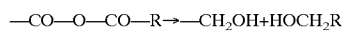

(E) Generation of a cyclic ether, a lactone and a diol from the cyclic carboxylic anhydride;

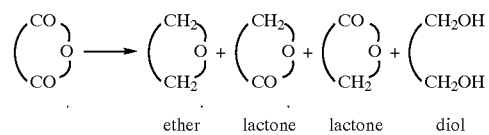

ether    lactone    lactone    diol

In this invention, in the case of aromatic carboxylic acids, not only hydrogenation of aromatic nucleus can be performed simultaneously with hydrogenation of the carboxyl group but also hydrogenation of only aromatic nucleus can also be carried out by selecting the catalyst and reaction conditions. For example, when terephthalic acid is hydrogenated in the presence of the R-Ru catalyst at a hydrogen pressure of 5 to 15 kg/cm$^2$, at a temperature of room temperature to 40° C., 1,4-cyclohexanedicarboxylic acid is obtained selectively (cf. Example 7 hereinbelow) whereas 1,4-cyclohexanedimethanol is obtained with Raney ruthenium and molybdenum-tin-modified Raney ruthenium are used together at a hydrogen pressure of up to 50 kg/cm$^2$ at a temperature of 60 to 160° C. (cf. Example 27 hereinbelow).

It is confirmed that generally speaking, when the same compound having an oxycarbonyl group is used, the reaction conditions used for preparing a compound having a methyleneoxy group (—CH$_2$—O—) with the noble Raney catalyst of this invention are different from the hydrogenation conditions with conventional Raney catalyst or carried type catalyst in that the catalyst of this invention works well at much lower hydrogen pressures or much lower reaction temperatures or requires much shorter reaction time than the conventional catalysts.

When compounds having an oxycarbonyl group are hydrogenated to produce compounds having a methyleneoxy group, use of the noble Raney catalysts of this invention results in conversion and selectivity higher than the conventional catalysts, so that the noble metal Raney catalysts of this invention reveal to be excellent.

3) Hydrogenation of aromatic nitrile compounds

Next, description will be made of a method for simultaneous hydrogenation of the aromatic ring and nitrile group of aromatic nitrile compounds to produce corresponding aminomethyl compounds.

The method, which proceeds as illustrated by the following reaction scheme:

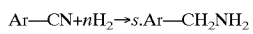

(wherein Ar is an aromatic ring, n is a stoichiometric number representing the amount of hydrogen required for hydrogenation, and s.Ar is Ar saturated with hydrogen), comprise reacting an aromatic nitrile compound, Ar—CN, with hydrogen in the presence of the hydrogenation catalyst according to this invention to reduce the aromatic ring, Ar, to a compound saturated with hydrogen, s.Ar, and at the same time reduce the nitrile group (—CN) to an aminomethyl group (—CH$_2$—NH$_2$) to produce an aminomethyl compound having a hydrogenated aromatic ring.

The aromatic nitrile compounds used in this invention are compounds having a ring which exhibits aromaticity on which at least one nitrile group is substituted. The number of nitrile group is not limited to 1 but the compounds may have a plurality of nitrile groups. Compounds having 1 to 3 nitrile groups are preferred.

The ring exhibiting aromaticity may be, for example, benzene ring, naphthalene ring, phenanthrene ring, azulene ring, pyridine ring, pyridazine ring, pyrimidine ring, pyrazine ring, triazine ring, quinoline ring, isoquinoline ring, quinoxaline ring, phthalazine ring, quinazoline ring, cinnoline ring, and the like. Ar used in this invention also includes assemblies of such rings or a plurality of rings connected through one or more divalent organic groups. Preferred are benzene ring, naphthalene ring, pyridine ring, and ring assemblies connected directly through simple bonds or indirectly through divalent groups such as a methylene group, —O—, etc. The aromatic rings may be substituted with one or more halogen atoms or organic groups such as acyclic alkyl groups, cyclic alkyl groups, and alkoxy groups.

Specific examples of the aromatic nitrile compounds include benzonitrile, phthalonitrile, isophthalonitrile, terephthalonitrile, 2-chlorobenzonitrile, 2-methylbenzonitrile, 3-methylbenzonitrile, 4-methylbenzonitrile, 4-ethoxybenzonitrile, 2-chloroterephthalonitrile, 4,4'-dicyanobiphenyl, 1-cyanonaphthalene, 2-cyanonaphthalene, 1,4-dicyanonaphthalene, 1,5-dicyanonaphthalene, 1,6-dicyano-naphthalene, 2,5-dicyanonaphthalene, 2,6-dicyanonaphthalene, 2-cyanopyridine, 3-cyanopyridine, 4-cyanopyridine, 2,5-dicyanopyridine and the like. Preferred are phthalonitrile, isophthalonitrile, terephthalonitrile, and 4,4'-dicyanobiphenyl.

The resulting aminomethyl compounds are compounds corresponding to aromatic cyano compounds used, for example, cyclohexylmethylamine when benzonitrile is used, 1,2-bis (aminomethyl) cyclohexane when isophthalonitrile is used, 4-aminomethylpiperidine when 4-cyanopyridine is used. Particularly, bis(aminomethyl)cyclohexane compounds corresponding to phthalonitrile, isophthalonitrile, and terephthalonitrile and derivatives thereof are useful as starting materials for polyamide resins and epoxy curing agents. Diisocyanates that can be readily derived from the bis(aminomethylcyclohexane compounds are useful, for example, as monomers for resins for manufacturing lenses.

The type of reaction may be any one of a liquid phase suspension reaction, a liquid phase fixed bed reaction and a gas phase reaction. The reaction may proceed in solvents or without solvents. When solvents are used, any solvent that is usually used in hydrogenation reactions can be used without limitation. Examples of preferred solvents include alcohol solvents, ether solvents, and the like. As the alcohol and ether solvents, there can be cited methanol, ethanol, isopropanol, n-butanol, cyclohexanol, ethylene glycol, 1,4-butanediol, ethylene glycol monomethyl ether, ethylene glycol monoethyl ether, diethylene glycol diethyl ether, triethylene glycol diethyl ether, dioxane, tetrahydrofuran, and the like. These solvents may be used singly or two or more of them may be used in admixture. Since addition of water in the solvent or reaction mixture increases yield and/or selectivity, water-containing organic solvents may be used with better results as the case may be.

In the method of this invention, increased reaction results may sometimes be obtained by addition of inorganic bases, for example, hydroxides, carbonates or alkoxides of alkali metals or alkaline earth metals singly or in combination of two or more of them.

In the method of this invention, the reaction temperature is within the range of room temperature to 200° C., preferably room temperature to 150° C. At temperatures below room temperature, no sufficient reaction rate can be obtained while no significant increase in the performance of the catalyst can be obtained at temperatures above 200° C. and, hence, use of such high temperatures is not only disadvantageous from economical viewpoints but also undesirable since aromatic cyano compounds having thermally unstable substituents tend to suffer from thermal decomposition.

The pressure upon hydrogenation reaction according to this invention is suitably 1 to 100 kg/cm2 as partial pressure of hydrogen. Sufficient result can be obtained particularly at a low pressure of several kg/cm$^2$ to 35 kg/cm$^2$.

The reaction time depends on the reaction temperature, pressure, the kind of the catalyst used, the reactivity of the compound to be hydrogenated, and the like but is not limited particularly as far as it is long enough for the objective reaction to be completed. Usually, the reaction time is about 1 to about 24 hours. The amount of catalyst used in the reaction is preferably 0.1 to 100 parts by weight per 100 parts by weight of the starting material for the reaction. However, it may be selected freely within the range where practically acceptable reaction rates can be obtained in accordance with various conditions including the reaction temperature or hydrogen pressure.

Hydrogen used in this invention does not have to be highly pure gas but may contain inert gases that do not affect the hydrogenation reaction significantly.

DESCRIPTION OF PREFERRED EMBODIMENTS

Hereafter, examples of noble metal Raney catalysts for hydrogenation and method for preparing hydrogenated compounds with such catalysts. However, this invention should not be construed as being limited thereto.

EXAMPLE 1

1—1: Preparation of Raney ruthenium catalyst

An alloy of Ru/Au=1/1 by weight was prepared from metallic Ru and Al by a button arc melting method in argon stream. The resulting R-Ru alloy was crushed and a fraction which passed 100 mesh was collected. 40 g of the R-Ru alloy powder was developed with 320 g of an aqueous 17% by weight sodium hydroxide solution. The developing temperature was set to 90° C. and the alloy powder was charged into the aqueous sodium hydroxide solution over 20 minutes. Thereafter, the mixture was kept at that temperature for 2 hours. These procedures were carried out in the atmosphere of nitrogen gas. After the development was completed, deaerated water was used for washing the alloy powder repeatedly by gradient method until the washings had a pH of 9.5. The R-Ru catalyst after the development was dipped in deaerated water for storage. 1–2: Hydrogenation of 1,4-diaminomethylbenzene A 100 ml autoclave made of stainless steel (SUS-316) equipped with a stirrer, a thermometer, and a small sintered stainless steel filter for extracting the reaction mixture after completion of the reaction was provided. The inside of the autoclave was purged with nitrogen gas and then 2.0 g of the R-Ru catalyst was charged therein. 30 g of deoxygenated deionized water, 6.03 g of 1,4-diaminomethyl-benzene and 2.85 g of NaOH were charged. The charging operations were performed with preventing the materials to be charged from contacting air as far as possible. Then, after the nitrogen gas in the gas phase in the autoclave was sufficiently purged with hydrogen gas, the hydrogen pressure was set to 10 kg/cm$^2$G at room temperature. While stirring well at room temperature, hydrogenation reaction was started. While monitoring the hydrogen gas absorption rate, hydrogen gas was supplied from gas bomb when a hydrogen pressure of 5 kg/cm$^2$ was reached to increase the hydrogen pressure to 10 kg/cm$^2$. Further, when a decrease in the hydrogen gas absorption rate was observed as compared with the initial hydrogen gas absorption rate, the reaction mixture was gradually heated. This reaction operation was repeated until absorption of hydrogen gas stopped. Consequently, the temperature was increased from room temperature to 62° C., and the hydrogenation reactions was completed in a reaction time of 5.5 hours. The reactions results were as follows. 1,4-Diaminomethylbenzene conversion was 100%, and yield of 1,4-diaminomethylcyclo-hexane of 90.4% by mole while yield of secondary amine was 0.6% by mole.

EXAMPLE 2

Hydrogenation of 1,4-diaminomethylbenzene

Hydrogenation reaction of 1,4-diaminomethylbenzene was performed in the same manner as in Example 1 except that the reaction temperature was increased from room temperature to 44° C. and the reaction time was 6.5 hours. The reaction results were as follows. 1,4-Diaminomethylbenzene conversion was 100%, and yield of 1,4-diaminomethylcyclo-hexane of 84.1% by mole while yield of secondary amine was 0.3% by mole. The hydrogenation reaction started from room temperature when absorption of hydrogen gas was already observed.

EXAMPLE 3

Hydrogenation of Pyridine

Hydrogenation of pyridine was performed in the same manner as in Example 1 except that 2.0 g of the R-Ru catalyst prepared in Example 1, 5.03 g of pyridine, and 30 g of deionized water were used, the reaction temperature was increased from room temperature to 40° C., and the reaction time was 1.3 hours. When the reaction started at room temperature, absorption of hydrogen gas was already observed. The reaction results were as follows. Pyridine conversion was 100%, and yield of piperidine was 99.8% by mole.

EXAMPLE 4

Hydrogenation of Aniline

Hydrogenation of aniline was performed in the same manner as in Example 1 except that 2.0 g of the R-Ru catalyst prepared in Example 1, 2.5 g of aniline, 15 g of deionized water, and 15 g of methanol were used, the reaction temperature was increased from room temperature to 85° C., and the reaction time was 2 hours. The reaction results were as follows. Aniline conversion was 100%, and yield of cyclohexylamine was 98.2% by mole.

EXAMPLE 5

Hydrogenation of Phenol

Hydrogenation of phenol was performed in the same manner as in Example 1 except that 2.0 g of the R-Ru catalyst prepared in Example 1, 2.5 g of phenol, 15 g of deionized water, and 15 g of methanol were used, the reaction temperature was from room temperature without an increase, and the reaction time was 0.7 hour. The reaction results were as follows. Phenol conversion was 100%, and yield of cyclohexanol was 99.8% by mole.

EXAMPLE 6

Hydrogenation of Terephthalic Acid

Hydrogenation of terephthalic acid was performed in the same manner as in Example 1 except that 1.0 g of the R-Ru catalyst prepared in Example 1, 2.33 g of terephthalic acid, 27.9 g of dioxane, and 3.1 g of deionized water were used, the reaction temperature was increased from room temperature to 40° C., and the reaction time was 9 hours. When the reaction started at room temperature, absorption of hydrogen gas was already observed. The reaction results were as follows. Terephthalic acid conversion was 100%, and yield of 1,4-cyclohexanedicarboxylic acid was 99.0% by mole.

EXAMPLE 7

Hydrogenation of 1,4-benzenedimethanol

Hydrogenation of 1,4-dimethanol was performed in the same manner as in Example 1 except that 2.0 g of the R-Ru catalyst prepared in Example 1, 5.0 g of 1,4-benzenedimethanol, 20 g of deionized water, and 10 g of methanol were used, the reaction temperature was increased from room temperature to 44° C., and the reaction time was 1.6 hours. When the reaction started at room temperature, absorption of hydrogen gas was already observed. The reaction results were as follows. 1,4-Benzenedimethanol conversion was 100%, and yield of 1,4-cyclohexanedimethanol was 80.8% by mole.

EXAMPLE 8

Hydrogenation of α-phenylethyl Alcohol

Hydrogenation of α-phenylethyl alcohol was performed in the same manner as in Example 1 except that 2.0 g of the R-Ru catalyst prepared in Example 1, 5.0 g of α-phenylethyl alcohol, 20 g of deionized water, and 10 g of methanol were used, the reaction temperature was room temperature without an increase, and the reaction time was 1.4 hours. The hydrogen gas absorption rate at room temperature was so high that elevation of temperature was unnecessary. The reaction results were as follows. α-Phenylethyl alcohol conversion was 100%, and yield of α-cyclohexylethyl alcohol was 97.0% by mole.

EXAMPLE 9

Hydrogenation of 2-naphthol

Hydrogenation of 2-naphthol was performed in the same manner as in Example 1 except that 2.0 g of the R-Ru catalyst prepared in Example 1, 2.0 g of 2-naphthol, 15 g of deionized water, and 15 g of methanol were used, the reaction temperature was increased from room temperature to 44° C., and the reaction time was 2.5 hours. When the reaction started at room temperature, absorption of hydrogen gas was already observed. The reaction results were as follows. 2—Naphthol conversion was 100%, and yield of decahydro-2-naphthol was 96.9% by mole.

EXAMPLE 10

Hydrogenation of 4,4'-diaminodiphenylmethane

Hydrogenation of 4,4'-diaminodiphenylmethane was performed in the same manner as in Example 1 except that 2.0 g of the R-Ru catalyst prepared in Example 1, 5.0 g of 4,4'-diaminodiphenylmethane, 30 g of dioxane, and 2 g of deionized water were used, the reaction temperature was increased from room temperature to 120° C., and the reaction time was 4.5 hours. When the reaction started at room temperature, absorption of hydrogen gas was already observed. The reaction results were as follows. 4,4'-Diaminodiphenylmethane conversion was 100%, and yield of 4,4,-diaminodicyclohexylmethane was 98.4% by mole.

EXAMPLE 11

Hydrogenation of 2-aminobiphenyl

Hydrogenation of 2-aminobiphenyl was performed in the same manner as in Example 1 except that 2.0 g of the R-Ru catalyst prepared in Example 1, 5.0 g of 2-aminobiphenyl, 20 g of deionized water, and 10 g of methanol were used, the reaction temperature was increased from room temperature to 100° C., and the reaction time was 3.4 hours. The reaction results were as follows. 2-Aminobiphenyl conversion was 100%, and yield of 2-bicyclohexylamine was 60% by mole.

EXAMPLE 12

Hydrogenation of 4-hydroxypyridine

Hydrogenation of 4-hydroxypyridine was performed in the same manner as in Example 1 except that 2.0 g of the R-Ru catalyst prepared in Example 1, 5.0 g of 4-hydroxypyridine, 15 g of deignized water, and 15 g of methanol were used, the reaction temperature was increased from room temperature to 40° C., and the reaction time was 1.7 hours. The reaction results were as follows. 4-Hydroxypyridine conversion was 100%, and yield of 4-hydroxypiperidine was 95% by mole.

EXAMPLE 13

Hydrogenation of Bisphenol A

Hydrogenation of bisphenol A was performed in the same manner as in Example 1 except that 2.0 g of the R-Ru catalyst prepared in Example 1, 5.0 g of bisphenol A, 30 g of dioxane, and 2.0 g of deionized water were used, the reaction temperature was room temperature, and the reaction time was 2.2 hours. The reaction results were as follows. Bisphenol A conversion was 100%, and yield of 4,4'-isopropylidenedicyclohexanol was 99.1% by mole.

EXAMPLE 14

14–1: Preparation of addition method tin-modified Raney ruthenium catalyst

In a 500 ml 4-necked glass flask was charged 315.6 g of aqueous 17% by weight so hydroxide solution under nitrogen gas atmosphere. To this was added 7.92 g of $Na2SnO_3.3H_2O$ while stirring. The mixture was dissolved at room temperature. Fine powder (40 g) of Raney ruthenium alloy (aluminum:ruthenium=50:50) which passed 100 mesh was added gradually over 30 minutes, which procedure involved abrupt heat generation and foaming. Hence, the flask was cooled on an ice bath to keep the temperature at 50 to 60° C., The mixture was stirred for continuous 15 minutes from the initiation of the addition until foaming stopped. Thereafter, the flask was dipped in an oil bath at 90° C. and stirring was continued for 2 hours. After the flask was cooled down to room temperature, deionized water purged with nitrogen was added to make 500 ml. After it was stirred, the mixture was decanted. Further, deionized water purged with nitrogen was added to make 500 ml, and the mixture was decanted after it was stirred. Then, the catalyst was transferred into a 300 ml vertical glass vessel having an inlet port for a liquid on the bottom and an outlet port for extracting a liquid on the top and deionized water purged with nitrogen was supplied from below at a rate of 2.5 liters/hour for 2 hours while stirring gently so that all the catalyst could float slowly and the liquid was extracted continuously from above to effect washing. As a result of the washing, pH value of the liquid decreased from 11.5 to 9.6. By the above-described procedure was obtained tin-modified Raney ruthenium catalyst. After development, the Raney ruthenium contained 92% of ruthenium and 8% of aluminum. The atomic ratio of tin/ruthenium of the tin-modified Raney ruthenium catalyst obtained by the procedure was 0.15.

14–2: Hydrogenation of adipic acid

In a 100 ml autoclave made of SUS316 were charged 27.9 g of dioxane and 3.1 g of water as a reaction solvent, and then 2.33 g of adipic acid. After the inside of the autoclave was purged with nitrogen, 1.0 g of the addition method tin-modified Raney ruthenium catalyst was added under nitrogen atmosphere. Then hydrogen gas was introduced into the autoclave until the inner pressure reached 50 $kg/cm^2$. The temperature was elevated until the inner temperature of the autoclave reached 160° C. and the reaction was carried out for 6 hours with stirring. After cooling down to room temperature, the pressure was returned to normal pressure, and the reaction mixture was taken out of the autoclave for analysis by liquid column chromatography. As a result, adipic acid conversion was 100%, yield of 1,6-hexanediol based on adipic acid was 78%, and yield of hydroxycaproic acid, which is an intermediate of hydrogenation, based on adipic acid was 16%.

Comparative Example 1

Reaction was performed in the same manner as in Example 14 except that the catalyst of Example 14 was replaced by a catalyst comprising 5% of ruthenium and 10% of tin carried on alumina. As a result, adipic acid conversion was 35%, yield of 1,6-hexanediol based on adipic acid was 1%, and yield of hydroxycaproic acid, an intermediate of hydrogenation, based on adipic acid was 30%.

EXAMPLE 15

15–1: Preparation of alloy method rhenium-modified Raney palladium catalyst

In the same manner as the preparation of Raney ruthenium alloy was prepared an alloy consisting of rhenium, palladium, and aluminum. The atomic ratio of rhenium metal to palladium metal was 0.1:1. The resulting alloy was developed with sodium hydroxide by the conventional method to obtain an alloy method rhenium-modified Raney palladium catalyst.

15-2: Hydrogenation of adipic acid

In a 100 ml autoclave made of SUS316 were charged 27.9 g of dioxane and 3.1 g of water as a reaction solvent, and then 2.33 g of adipic acid. After the inside of the autoclave was purged with nitrogen, 1.0 g of the alloy method rhenium-modified Raney palladium catalyst was added under nitrogen atmosphere. Then hydrogen gas was introduced into the autoclave until the inner pressure reached 50 kg/cm$^2$. The temperature was elevated until the inner temperature of the autoclave reached 210° C. and the reaction was carried out for 3 hours with stirring. After cooling down to room temperature, the pressure was returned to normal pressure, and the reaction mixture was taken out of the autoclave for analysis by liquid column chromatography. As a result,-adipic acid conversion was 100%, yield of 1,6-hexanediol based on adipic acid was 37%, and yield of hydroxycaproic acid, which is an intermediate of hydrogenation, based on adipic acid was 48%.

Comparative Example 2

Reaction was performed in the same manner as in Example 15 except that the catalyst of Example 15 was replaced by a catalyst comprising 5% of palladium and 1% of rhenium carried on silica. As a result, adipic acid conversion was 64%, yield of 1,6-hexanediol based on adipic acid was 14%, and yield of hydroxycaproic acid, an intermediate of hydrogenation, based on adipic acid was 37%.

EXAMPLE 16

16-1: Preparation of addition method tin-molybdenum-modified Raney ruthenium catalyst The same procedure as in Example 14 was repeated except that 7.0 g of $(NH_4)_6Mo_7O_{24}\cdot 4H_2O$ was added to Na2SnO3–3H$_2$O in the preparation of the addition method tin-modified Raney ruthenium catalyst in Example 14.

16-2: Hydrogenation of adipic acid

In a 100 ml autoclave made of SUS316 were charged 31 g of water as a reaction solvent and then 2.33 g of adipic acid. After the inside of the autoclave was purged with nitrogen, 1.0 g of the alloy method rhenium-modified Raney palladium catalyst was added under nitrogen atmosphere. Then hydrogen gas was introduced into the autoclave until the inner pressure reached 50 kg/cm$^2$. The temperature was elevated until the inner temperature of the autoclave reached 140° C. and the reaction was carried out for 2 hours with stirring. After cooling down to room temperature, the pressure was returned to normal pressure, and the reaction mixture was taken out of the autoclave for analysis by liquid column chromatography. As a result, adipic acid conversion was 99% and yield of 1,6-hexanediol based on adipic acid was 96%. In addition, 3% of 1-hexanol was by-produced.

EXAMPLE 17

Hydrogenation of Benzoic Acid

In a 100 ml autoclave made of SUS316 were charged 27.9 g of dioxane and 3.1 g of water as a reaction solvent, and then 2.33 g of benzoic acid. After the inside of the autoclave was purged with nitrogen, 1.0 g of the R-Ru catalyst obtained in Example 1 was added under nitrogen atmosphere. Then, hydrogen gas was introduced into the autoclave until the inner pressure reached 50 kg/cm$^2$. The temperature was elevated until the inner temperature of the autoclave reached 120° C. and the reaction was carried out for 2 hours with stirring. After cooling down to room temperature, the pressure was returned to normal pressure, and the reaction mixture was taken out of the autoclave for analysis by liquid column chromatography. As a result, benzoic acid conversion was 100%, yield of cyclohexanemethanol based on benzoic acid was 22%, and yield of cyclohexanecarboxylic acid, which is an intermediate of hydrogenation, based on benzoic acid was 77%.

EXAMPLE 18

Hydrogenation of Terephthalic Acid

In a 100 ml autoclave made of SUS316 were charged 27.9 g of dioxane and 3.1 g of water as a reaction solvent, and then 2.33 g of terephthalic acid. After the inside of the autoclave was purged with nitrogen, 1.0 g of the addition method tin-modified Raney ruthenium catalyst prepared in the same manner as in Example 14 was added under nitrogen atmosphere. Then hydrogen gas was introduced into the autoclave until the inner pressure reached 50 kg/cm$^2$. The temperature was elevated until the inner temperature of the autoclave reached 160° C. and the reaction was carried out for 3 hours with stirring. After cooling down to room temperature, the pressure was returned to normal pressure, and the reaction mixture was taken out of the autoclave for analysis by liquid column chromatography. As a result, terephthalic acid conversion was 100%, yield of cyclohexanedicarboxylic acid, which is a compound obtained by hydrogenation of the aromatic ring of terephthalic acid, based on terephthalic acid was 30%, and yield of 4-hydroxymethyl-cyclohexanecarboxylic acid, which is a compound obtained by one of the carboxylic groups of cyclohexanedicarboxylic acid was hydrogenated, based on terephthalic acid was 54% while yield of 1,4-cyclohexanedimethanol, which is a compound obtained by hydrogenation of the two carboxylic groups of cyclohexanedicarboxylic acid, based on terephthalic acid was 12%.

EXAMPLE 19

Hydrogenation of 1,4-cyclohexanedicarboxylic Acid

In a 100 ml autoclave made of SUS316 were charged 27.9 g of dioxane and 3.1 g of water as a reaction solvent, and then 2.41 g of 1,4-cyclohexanedicarboxylic acid. After the inside of the autoclave was purged with nitrogen, 1.0 g of the addition method tin-modified Raney ruthenium catalyst prepared in the same manner as in Example 14 was added under nitrogen atmosphere. Then hydrogen gas was introduced into the autoclave until the inner pressure reached 50 kg/cm$^2$. The temperature was elevated until the inner temperature of the autoclave reached 160° C. and the reaction was carried out for 3 hours with stirring. After cooling down to room temperature, the pressure was returned to normal pressure, and the reaction mixture was taken out of the autoclave. Cyclohexanedicarboxylic acid was analyzed by liquid column chromatography while the product was analyzed by gas chromatography. As a result, 1,4-cyclohexanedicarboxylic acid conversion was 100%, yield of cyclohexanedimethanol based on 1,4-cyclohexanedicarboxylic acid was 94.1%.

EXAMPLE 20

Hydrogenation of Maleic Anhydride

In a 100 ml autoclave made of SUS316 were charged 27.9 g of dioxane and 3.1 g of water as a reaction solvent, and then 2.33 g of maleic anhydride. After the inside of the autoclave was purged with nitrogen, 1.0 g of the addition method tin-modified Raney ruthenium catalyst prepared in the same manner as in Example 14 was added under nitrogen atmosphere. Then hydrogen gas was introduced into the autoclave until the inner pressure reached 50 kg/cm². The temperature was elevated until the inner temperature of the autoclave reached 160° C. and the reaction-was carried out for 3hours with stirring. After cooling down to room temperature, the pressure was returned to normal pressure, and the reaction mixture was taken out of the autoclave for analysis by liquid column chromatography. As a result, yield of γ-butyrolactone was 62%, that of 1,4-butanediol was 12% and that of tetrahydrofuran was 0.4%, based on maleic anhydride.

EXAMPLE 21 to 25

Preparation of Addition Method Various Metal-modified Raney Ruthenium and Hydrogenation of Adipic Acid Upon development of the R-Ru alloy, one of Pb(OAc)$_2$.3H$_2$O, In(NO$_3$)$_3$.3H$_2$O, Nb(OC$_2$H$_5$)$_5$, (NH$_4$)$_6$Mo$_{24}$.4H$_2$O, and (NH$_4$)$_{10}$W$_{12}$O$_{41}$.5H$_2$O was allowed to coexist to produce lead-modified Raney ruthenium, indium-modified Raney ruthenium, niobium-modified Raney ruthenium, molybdenum-modified Raney ruthenium, and tungsten-modified Raney ruthenium catalysts in the same manner as the addition method tin-modified Raney ruthenium catalyst.

In a 100 ml autoclave made of SUS316 were charged 27.9 g of dioxane and 3.1 g of water as a reaction solvent, and then 2.33 g of adipic acid. After the inside of the autoclave was purged with nitrogen, 1.0 g of each of the addition method lead-modified Raney ruthenium, indium-modified Raney ruthenium, niobium-modified Raney ruthenium, molybdenum-modified Raney ruthenium, and tungsten-modified Raney ruthenium catalysts was added under nitrogen atmosphere. Then hydrogen gas was introduced into the autoclave until the inner pressure reached 50 kg/cm². The inner temperature of the autoclave was set to the temperature described in Table 1 and reaction was performed for a predetermined time. After cooling down to room temperature, the pressure was returned to normal pressure, and the reaction mixture was taken out of the autoclave for analysis by liquid column chromatography. Table 1 shows conversion (%) based on adipic acid, yield of 1,6-hexanediol (HDO) and yield of hydroxycaproic acid (HCA).

TABLE 1

| Example | Additional Element | Temperature (° C.) | Time (hrs) | Conversion (%) | Yield of HDO | Yield of HCA |
|---|---|---|---|---|---|---|
| 21 | Pb | 140 | 3 | 29 | 2 | 19 |
| 22 | In | 160 | 3 | 50 | 1 | 18 |
| 23 | Nb | 100 | 3 | 94 | 25 | 47 |
| 24 | Mo | 120 | 2 | 100 | 57 | 5 |
| 25 | W | 110 | 1 | 100 | 22 | 19 |

EXAMPLE 26

Hydrogenation of Dimethyl Adipate

In a 100 ml autoclave made of SUS316 were charged 27.9 g of dioxane and 3.1 g of water as a reaction solvent, and then 2.33 g of dimethyl adipate. After the inside of the autoclave was purged with nitrogen, 1.0 g of the addition method tin-modified Raney ruthenium catalyst prepared in the same manner as in Example 14 was added under nitrogen atmosphere. Then hydrogen gas was introduced into the autoclave until th e inner pressure reached 50 kg/cm². The temperature was elevated until the inner temperature of the autoclave reached 160° C. and the reaction was carried out for 6 hours with stirring. After cooling down to room temperature, the pressure was returned to normal pressure, and the reaction mixture was taken out of the autoclave for analysis by liquid column chromatography.

As a result, dimethyl adipate conversion was 47%, yield of 1,6-hexanediol based on dimethyl adipate was 18%, and yield of hydroxycaproic acid methyl ester, which is an intermediate of hydrogenation, based on dimethyl adipate was 25%.

EXAMPLE 27

Hydrogenation of Terephthalic Acid

In a 100 ml autoclave made of SUS316 were charged 27.9 g of dioxane and 3.1 g of water as a reaction solvent, and then 2.33 g of terephthalic acid. After the inside of the autoclave was purged with nitrogen, 0.05 g of R-Ru catalyst and 0.95 g of the addition method molybdenum-tin-modified Raney ruthenium catalyst prepared in the same manner as in Example 16 was added under nitrogen atmosphere. Then hydrogen gas was introduced into the autoclave until the inner pressure reached 50 kg/cm². The temperature was elevated until the inner temperature of the autoclave reached 60° C. and the reaction mixture was stirred for 6 hours. Then, the inner temperature was elevated to 160° C. and the reaction was continued for 4 hours with stirring. After cooling down to room temperature, the pressure was returned to normal pressure, and the reaction mixture was taken out of the autoclave for analysis by liquid column chromatography. As a result, terephthalic acid conversion was 100%, yield of cyclohexanedimethanol, which is a compound obtained by hydrogenation of the aromatic ring and the carboxyl groups of terephthalic acid, based on terephthalic acid was 70.5%.

EXAMPLE 28

Hydrogenation of Terephthalonitrile

In a 100 ml autoclave made of SUS316 were charged 30 ml of dioxane, 2 ml of water, 3 g of terephthalonitrile, 0.02 g of sodium hydroxide, and 2 g of the R-Ru catalyst obtained in Example 1 and the hydrogen pressure was set to 10 kg/cm² at room temperature. Hydrogenation reaction was started with sufficient stirring at room temperature. The temperature was gradually elevated to a final temperature of 90° C. During temperature elevation and after the temperature reached 90° C., the hydrogen absorption rate was monitored. when the hydrogen pressure reached 5 kg/cm², the hydrogen pressure was returned to 10 kg/cm². This operation was repeated until hydrogen pressure drop in 10 minutes became 0.3 kg/cm² as a temporary target when the reaction was stopped. The catalyst was removed by filtration and the reaction mixture was analyzed by gas chromatography using an inner standard method. As a result, terephthalonitrile conversion was 99% or more, and yield of 1,4-bisaminomethylcyclohexane was 73%.

EXAMPLE 29

Hydrogenation of Isophthalonitrile

Reaction was performed in the same manner as in Example 28 except that isophthalonitrile was used instead of terephthalonitrile and no sodium hydroxide was added. isophthalonitrile conversion was 99% or more, and yield of 1,3-bis(aminomethyl)cyclohexane was 58%.

EXAMPLE 30

Hydrogenation of 4-cyanopyridine

Reaction was performed in the same manner as in Example 28 except that 4-cyanopyridine was used instead of terephthalonitrile and no sodium hydroxide was added. 4-cyanopyridine conversion was 99% or more, and yield of 4-aminomethylpiperidine was 80%.

What is claimed is:

1. A method for preparing a compound with a hydrogenated ring in the molecule comprising reacting a compound with an aromaticity-exhibiting ring in the molecule with hydrogen in the presence of a noble metal Raney catalyst comprising at least 50% by weight of ruthenium as an active ingredient of the catalyst.

2. The method as claimed in claim 1, wherein said noble metal Raney catalyst comprises at least one other metal element in addition to said ruthenium.

3. The method as claimed in claim 1, wherein said noble metal Raney catalyst comprises a mixture of
   (1) a noble metal Raney catalyst comprising at least 50% by weight ruthenium and
   (2) a noble metal Raney catalyst comprising at least 50% by weight ruthenium and at least one other metal element in addition to said ruthenium.

4. The method as claimed in claim 1, wherein said reacting is conducted at a pressure of 5 to 30 $kg/cm^2$ and a temperature of room temperature to 130° C.

* * * * *